(12) United States Patent
Maskara et al.

(10) Patent No.: US 8,676,314 B2
(45) Date of Patent: Mar. 18, 2014

(54) METHOD AND APPARATUS TO ENSURE CONSISTENT LEFT VENTRICULAR PACING

(75) Inventors: Barun Maskara, Blaine, MN (US);
Jiang Ding, Shoreview, MN (US); M. Jason Brooke, Woodstock, MD (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 570 days.

(21) Appl. No.: 12/435,915

(22) Filed: May 5, 2009

(65) Prior Publication Data

US 2009/0281590 A1    Nov. 12, 2009

Related U.S. Application Data

(60) Provisional application No. 61/126,859, filed on May 7, 2008.

(51) Int. Cl.
*A61N 1/00* (2006.01)

(52) U.S. Cl.
USPC .......................................................... 607/9

(58) Field of Classification Search
USPC .......................................................... 607/9
See application file for complete search history.

(56) References Cited

U.S. PATENT DOCUMENTS

| | | |
|---|---|---|
| 4,991,583 A | 2/1991 | Silvian |
| 5,222,493 A | 6/1993 | Sholder et al. |
| 5,324,310 A | 6/1994 | Greeninger et al. |
| 5,350,410 A | 9/1994 | Kleks et al. |
| 5,514,163 A | 5/1996 | Markowitz et al. |
| 5,601,615 A | 2/1997 | Markowitz et al. |
| 5,741,308 A | 4/1998 | Sholder |
| 5,749,906 A | 5/1998 | Kieval |
| 5,902,324 A | 5/1999 | Thompson et al. |
| 6,038,474 A | 3/2000 | Zhu et al. |
| 6,480,742 B2 | 11/2002 | Stahmann et al. |
| 6,574,506 B2 | 6/2003 | Kramer et al. |
| 6,871,096 B2 | 3/2005 | Hill |
| 7,123,960 B2 | 10/2006 | Ding et al. |
| 7,130,688 B2 | 10/2006 | Stahmann et al. |
| 7,142,915 B2 | 11/2006 | Kramer et al. |
| 7,158,828 B2 | 1/2007 | Kramer et al. |
| 7,181,284 B2 | 2/2007 | Burnes |

(Continued)

FOREIGN PATENT DOCUMENTS

| | | |
|---|---|---|
| EP | 0882469 | 9/1998 |
| EP | 1995685 | 11/2008 |
| WO | WO0071202 | 11/2000 |
| WO | WO2005089865 | 9/2005 |

*Primary Examiner* — Christopher D Koharski
*Assistant Examiner* — Philip Edwards
(74) *Attorney, Agent, or Firm* — Brooks, Cameron & Huebsch, PLLC

(57) ABSTRACT

A method of operating a cardiac therapy system to deliver cardiac resynchronization therapy (CRT) pacing that includes pacing both ventricles or pacing only the left ventricle is described. Delivery of the CRT pacing to one or both ventricles is scheduled for a cardiac cycle. If an intrinsic depolarization of a ventricle is detected during a pacing delay of the ventricle, then the scheduled CRT pacing to the ventricle is inhibited for the cycle. The intrinsic interval of the ventricle, such as the intrinsic atrioventricular interval concluded by the intrinsic depolarization, is measured. During a subsequent cardiac cycle, the pacing delay of the ventricle is decreased to be less than or equal to the measured intrinsic interval. Capture of the ventricle is verified after pacing is delivered during the subsequent cardiac cycle.

30 Claims, 9 Drawing Sheets

(56) References Cited

U.S. PATENT DOCUMENTS

| | | |
|---|---|---|
| 7,248,925 B2 | 7/2007 | Bruhns |
| 7,254,442 B2 | 8/2007 | Van Gelder |
| 7,392,083 B2 | 6/2008 | Kramer et al. |
| 7,512,441 B2 | 3/2009 | Zhang |
| 7,680,535 B2 | 3/2010 | Stahmann et al. |
| 2001/0031990 A1 | 10/2001 | Zhang |
| 2002/0161410 A1* | 10/2002 | Kramer et al. .............. 607/9 |
| 2005/0209650 A1 | 9/2005 | Van Gelder et al. |
| 2006/0224198 A1* | 10/2006 | Dong et al. ................ 607/9 |
| 2006/0235478 A1 | 10/2006 | Van Gelder |
| 2007/0043396 A1 | 2/2007 | Stahmann et al. |
| 2008/0004668 A1 | 1/2008 | Kadhiresan et al. |
| 2009/0281590 A1 | 11/2009 | Maskara et al. |
| 2012/0158084 A1 | 6/2012 | Stahmann et al. |

\* cited by examiner

| | Measured AVI$_R$ | Measured AVI$_L$ | Current AVD | Optimized AVD |
|---|---|---|---|---|
| MTR | 120 | 150 | 150 | 100 |
| Rate 8 | 125 | 155 | 150 | 100 |
| Rate 7 | 135 | 165 | 150 | 110 |
| Rate 6 | 150 | 180 | 150 | 120 |
| Rate 5 | 155 | 180 | 150 | 120 |
| Rate 4 | 170 | 200 | 150 | 140 |
| Rate 3 | 180 | 200 | 150 | 150 |
| Rate 2 | 190 | 220 | 150 | 160 |
| LRL | 220 | 240 | 150 | 190 |

Figure 6

METHOD AND APPARATUS TO ENSURE CONSISTENT LEFT VENTRICULAR PACING

RELATED APPLICATION

This application claims the benefit of Provisional Patent Application Ser. No. 61/126,859 filed on May 7, 2008, to which priority is claimed pursuant to 35 U.S.C. §119(e) and which is hereby incorporated herein by reference in its entirety.

FIELD OF THE INVENTION

The present invention relates generally to cardiac pacing therapy, and more specifically, to methods and systems for determination of pacing parameters to ensure consistent capture for left ventricular pacing during cardiac resynchronization therapy.

BACKGROUND OF THE INVENTION

Congestive heart failure is the loss of pumping power of the heart, resulting in the inability to deliver enough blood to meet the demands of peripheral tissues. Congestive heart failure (CHF) may cause weakness, loss of breath, and build up of fluids in the lungs and other body tissues.

CHF is usually a chronic, long term condition, but can occur suddenly. It may affect the left heart, right heart or both sides of the heart. Heart failure has a variety of causes, primarily ischemic heart disease. The deterioration of the muscles of the heart caused by ischemic heart disease result in an enlargement of the heart and reduced contractility. The reduced contractility decreases the cardiac output of blood and typically results in an increased heart rate. Cardiac conduction path block may also occur in the enlarged heart tissue, causing the signals that control the heart rhythm to travel more slowly through the enlarged heart tissue. For example, if CHF affects the left ventricle, signals that control the left ventricular contraction are delayed, and the left and right ventricles do not contract simultaneously. Non-simultaneous contractions of the left and right ventricles decrease the pumping efficiency of the heart.

CHF may be treated by medication and/or by cardiac pacing therapy. Pacing therapy to promote synchronization of heart chamber contractions for improved cardiac function is generally referred to as cardiac resynchronization therapy (CRT). Some cardiac pacemakers are capable of delivering CRT by pacing multiple heart chambers. Pacing pulses are delivered to the heart chambers in a sequence that causes the heart chambers to contract with enhanced synchrony, increasing the pumping power of the heart and delivering more blood to the peripheral tissues of the body. In the case of dysynchrony of right and left ventricular contractions, a CRT pacing may be used to resynchronize the left and right ventricles. Successful pacing of the left ventricle is critical to achieve the benefit of CRT. Bi-atrial pacing or pacing of all four heart chambers may also be used.

Pacing therapy is delivered by pacing one or more heart chambers using pacing delays that control the timing and sequence of the pacing pulses. Appropriate specification of these pacing delays is desirable to achieve improvement of cardiac function through enhanced synchrony. For the reasons stated above, and for other reasons stated below which will become apparent to those skilled in the art upon reading the present specification, there is a need in the art for methods and systems that provide for determination of delays used for CRT pacing. The present invention fulfills these and other needs.

SUMMARY OF THE INVENTION

The present invention is directed to systems and methods for determining cardiac pacing parameters for cardiac resynchronization therapy (CRT) pacing includes at least pacing a left ventricle.

One embodiment of the invention involves a method of operating a cardiac therapy system to deliver cardiac resynchronization therapy (CRT) pacing that includes pacing both ventricles or pacing only the left ventricle. Delivery of the CRT pacing to one or both ventricles is scheduled for a cardiac cycle. If an intrinsic depolarization of a ventricle is detected during a pacing delay of the ventricle, then the scheduled CRT pacing to the ventricle is inhibited for the cycle. The intrinsic interval of the ventricle, e.g., the intrinsic atrioventricular interval concluded by the intrinsic depolarization, is measured. During a subsequent cardiac cycle, the pacing delay of the ventricle is decreased to be less than or equal to the measured intrinsic interval. Capture of the ventricle is verified after pacing is delivered during the subsequent cardiac cycle.

According to various aspects of the invention, the pacing delay may involve one or more of a right atrioventricular delay, a left atrioventricular delay, and an interventricular delay.

The pacing delay may remain at the decreased value for a number of subsequent cardiac cycles or may be further decreased if capture is not verified for subsequent cycles. If capture is confirmed, the pacing delay may be gradually increased, e.g., incrementally increased by a predetermined amount, during one or more subsequent cardiac cycles.

According to one implementation, the CRT pacing is scheduled to be delivered to both left and right ventricles. The CRT pacing to the left or right ventricles may be inhibited by an intrinsic depolarization that occurs during the pacing delay of that ventricle. For example, a scheduled right ventricular pace may be inhibited by an intrinsic right ventricular depolarization that occurs during a right ventricular pacing delay. A scheduled left ventricular pace may be inhibited by an intrinsic left ventricular depolarization that occurs during a left ventricular pacing delay. Paces to both the left and right ventricles may be inhibited if intrinsic depolarizations of both ventricles occur during their respective pacing delays. If pacing is inhibited to a ventricle, the intrinsic interval of that ventricle is measured. A subsequent pacing delay for the ventricle is decreased based on the intrinsic interval measured for that ventricle.

According to a further aspect, if no intrinsic depolarization of the ventricle is detected during the pacing delay, then the CRT pacing is delivered as scheduled. A cardiac response to the pacing (e.g., capture, fusion, or non-capture of the ventricle with or without intrinsic activation) is determined. The pacing delay of the ventricle is adjusted for the subsequent cardiac cycle based on the cardiac pacing response. For example, the same pacing delay may be maintained on subsequent cardiac cycles so long as capture is detected. In another implementation, the pacing delay may be increased during subsequent cycles if capture is detected and the pacing delay was previously decreased responsive to detection of an intrinsic depolarization. If fusion is detected, the pacing delay may be incrementally decreased. If non-capture is detected, one or more pacing parameters affecting pacing energy output (e.g., current, voltage, pulse duration, and/or pulse waveform) may be adjusted.

According to a further aspect, cardiac rate may be measured, for example, by measuring the intrinsic atrial rate. The pacing delay may be adjusted based on both the cardiac pacing response and measured cardiac rate. In one implementation, adjusting the pacing delay comprises adjusting the pacing delay using a look-up table of pacing delays indexed by cardiac rate. The pacing delay values obtained from the look up table may be additionally increased or decreased beat by beat basis according to whether an intrinsic depolarization occurred during the previous cardiac cycle and/or on the capture status of a previous cycle.

Another embodiment of the invention involves a method of setting pacing delays for cardiac resynchronization therapy (CRT) pacing that includes presentation of information to a human analyst regarding relationships between the pacing delays, measured cardiac rate, measured intrinsic interval and the cardiac pacing response for a plurality of cardiac intervals. These parameters are determined for a plurality of cardiac intervals and are stored. The stored information is analyzed to determine at least one recommended pacing delay. The at least one recommended pacing delay is presented to a human analyst via a user interface.

According to one implementation, the stored information may be analyzed to develop a look up table of recommended pacing delays based on the previous pacing delays, measured cardiac rate, the measured intrinsic interval; and/or the cardiac pacing response for the plurality of cardiac intervals.

Yet another embodiment of the invention is directed to a cardiac therapy system capable of delivering cardiac resynchronization therapy (CRT) pacing that involves pacing at least the left ventricle. The system includes electrodes configured to electrically couple to right and left ventricles. Sensing circuitry is coupled to the electrodes and is configured to sense intrinsic depolarization signals and other cardiac signals via the electrodes. Pacing circuitry is configured to generate pacing pulses deliverable through the electrodes. The system includes cardiac response classification circuitry that is capable of determining a cardiac response to the pacing pulses. The system also includes pacing control circuitry that schedules pacing to be delivered relative a pacing delay to at least one ventricle during a cardiac cycle. If an intrinsic depolarization is detected during the pacing delay, the scheduled CRT pacing to the ventricle is inhibited. If an intrinsic depolarization occurs during the pacing delay, the intrinsic interval (e.g., atrioventricular interval or interventricular interval that is initiated or concluded by the intrinsic depolarization) is measured. The pacing delay of a subsequent cardiac cycle is decreased to be less than or equal to the measured intrinsic interval.

For example, if the pacing control circuitry schedules delivery of CRT pacing to both left and right ventricles, one or both of the paces may be inhibited by intrinsic depolarizations occurring within the respective pacing delays of the left and right ventricles. If either pace is inhibited, the intrinsic interval for that ventricle is measured and is used to decrease subsequent pacing delays for that ventricle. If both paces are inhibited, the intrinsic intervals for both ventricles may be measured and used to decrease subsequent pacing delays for the ventricles.

The pacing control circuitry may further decrease the pacing delay for a ventricle during subsequent cardiac cycles until the cardiac response classification circuitry determines that capture occurs. When capture is detected, the pacing control circuitry may increase the pacing delay for each subsequent cycle until the initial pacing delay is achieved.

If an intrinsic depolarization of the ventricle is not detected during the pacing delay of the cardiac cycle, the CRT pacing is delivered as scheduled. During subsequent cardiac cycles, a pacing delay for a ventricle may be based on the cardiac pacing response of that ventricle to the delivered CRT pacing. For example, the cardiac response classification processor may discriminate between capture, fusion, and non-capture of the ventricle. The pacing delay of the ventricle for the subsequent cardiac cycle is adjusted based on the cardiac pacing response. In one implementation, if capture is detected as the pacing response, the pacing delay may be maintained at the same value for subsequent cycles. If fusion is determined to be the pacing response, the pacing delay may be incrementally decreased for subsequent cycles to avoid fusion responses.

The cardiac therapy system may also include a memory in which information such as measured cardiac rate, measured intrinsic intervals, and cardiac pacing response for a plurality of cardiac cycles is stored. The pacing control circuitry, which may be fully implantable, or may have internal and external components operating in cooperation, may analyze the stored information to determine one or more pacing delays for the CRT pacing. The analysis may take into account one or more of previous pacing delays, the measured cardiac rate, the measured intrinsic intervals, and the cardiac pacing responses of one or both ventricles for the plurality of cardiac cycles.

In one implementation, the cardiac therapy system includes a memory configured to store information related to the measured cardiac rate, the measured intrinsic interval, and the cardiac pacing response for a plurality of cardiac intervals. The memory may store a look up table used to adjust pacing delays beat by beat. The system may also include an external user interface configured to present to a human analyst information indicating relationships between the previous pacing delays, measured cardiac rates, the measured intrinsic intervals and/or the cardiac pacing responses for the plurality of cardiac intervals. The pacing control circuitry may analyze the information stored in the memory to determine at least one recommended pacing delay for a subsequent cardiac cycle. One or more recommended pacing delays can presented to a human analyst via a user interface to allow the human analyst to accept or override the recommended pacing delays. The recommended pacing delays may be one or more of right atrioventricular delay, a left atrioventricular delay, and an interventricular delay.

The cardiac therapy system may also include a sensor configured to generate an output based a patient's hemodynamic need. The pacing control circuitry may adjust the pacing delay based on the sensor output, thus taking into account the patient's hemodynamic need when adjusting the pacing delay.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 6 illustrates a user interface component that may be operated by a user to confirm suggested pacing delays or to adjust pacing delays in accordance with embodiments of the invention;

Figure 1A:
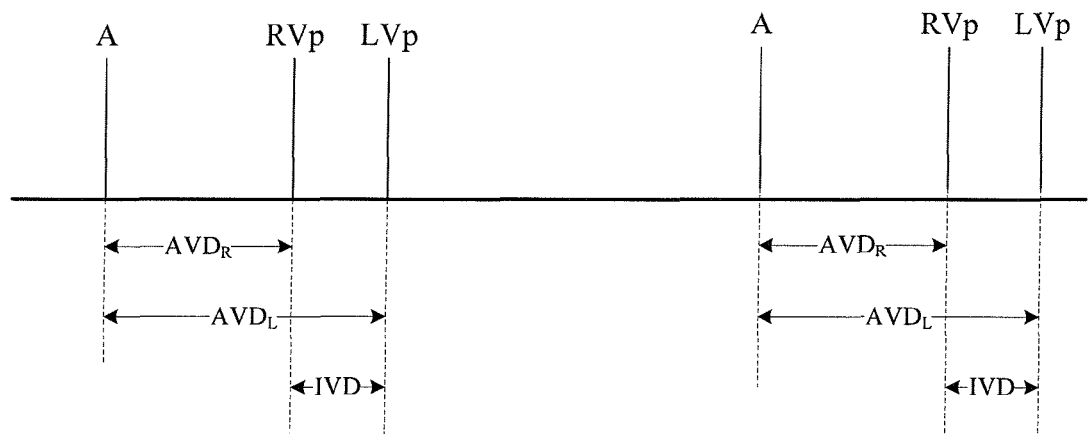
FIGS. 1A and 1B are timing diagrams illustrating pacing delays for atrial tracking or atrioventricular sequential CRT pacing.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described hereinbelow. For example, a device or system may be implemented to include one or more of the advantageous features and/or processes described below. It is intended that such device or system need not include all of the features described herein, but may be implemented to include selected features that provide for useful structures and/or functionality. Such a device or system may be implemented to provide a variety of therapeutic or diagnostic functions.

Embodiments of the invention are directed to systems and methods for ensuring or promoting consistent ventricular pacing through adjustment of ventricular pacing delays and/or pacing energy parameters. Adjustment of the pacing delays may involve adjusting one or more atrioventricular delays and/or interventricular delay, for example. Adjustment of the pacing energy parameters may involve adjusting one or more of the voltage, current, duration, and/or waveform of the pacing pulses. The techniques described herein are particularly useful for setting pacing delays and/or pacing energy to enhance delivery of cardiac resynchronization pacing therapy (CRT).

CRT involves pacing stimulation applied to one or more heart chambers in a manner that compensates for conduction delays and improves pumping action. CRT may involve pacing one or both atria and/or one or both ventricles. For example, when CRT pacing is applied to one or both ventricles, a more coordinated contraction of the ventricles is achieved with improved pumping efficiency and increased cardiac output. CRT can be implemented in certain patients by pacing in both left and right ventricles, or in the left ventricle (LV) or the right ventricle (RV) alone. For example, in some CRT configurations, an RV pace may be delivered following an appropriate pacing delay relative an atrial sense or pace and an LV pace may be delivered after an appropriate delay initiated relative to a right ventricular (RV) or pace or sense or may be delivered after an appropriate delay initiated relative to the atrial sense or pace. In some configurations, resynchronization pacing may involve biventricular pacing with the paces to right and left ventricles delivered either simultaneously or sequentially, with an interventricular delay (IVD) between the paces. The IVD is sometimes referred to as a biventricular offset or LV offset In one example of CRT, atrial paces and senses trigger an atrioventricular delay ($AVD_R$) which upon expiration results in a pace to the right ventricle. A pace to the left ventricular is delivered at the specified IVD with respect to expiration of the $AVD_R$. This pacing scenario may alternatively be described in terms of atrioventricular delays between the atrial sense or pace and the scheduled pace to the right ventricle ($AVD_R$) and a separate atrioventricular delay ($AVD_L$) which occurs between an atrial sense or pace and the scheduled pace to the left ventricle.

CRT pacing is often implemented in an inhibited demand mode wherein a pacing pulse is delivered to a cardiac chamber if no intrinsic beat is detected in the cardiac chamber prior to expiration of a pacing interval. In ventricular CRT pacing, ventricular pacing is typically applied to both ventricles, although in some implementations only one ventricle, such as the LV, may be paced. In some implementations, CRT pacing involving biventricular pacing or LV only pacing may be implemented in atrial tracking or AV sequential pacing modes. In these pacing modes, a sense or pace initiates an atrioventricular delay and, if no intrinsic ventricular depolarization is sensed prior to expiration of the atrioventricular delay, ventricular pacing is delivered.

Figure 1B:
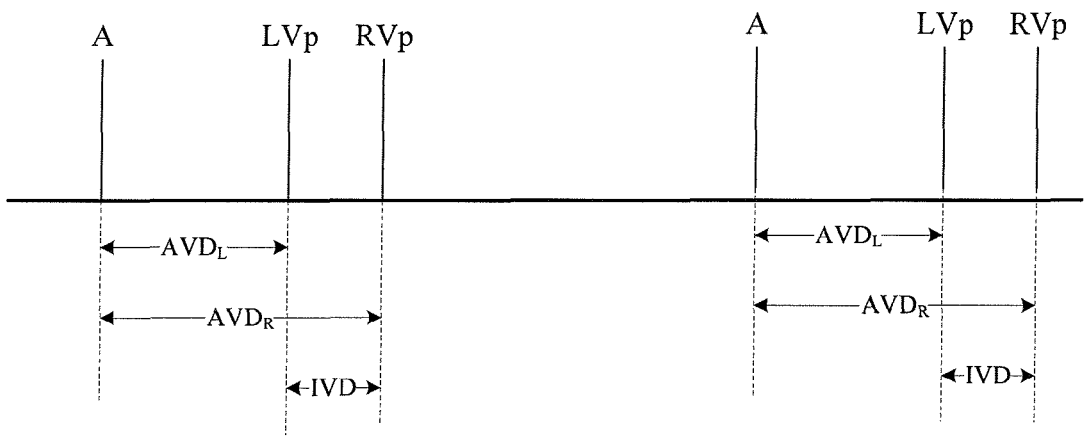

An $AVD_R$ and $AVD_L$ having the same duration during a cardiac cycle results in simultaneous pacing of the right and left ventricles. If the duration of the $AVD_R$ is different from the duration of the $AVD_L$, the result is pacing with an interventricular delay (IVD) which is the difference between the $AVD_L$ and the $AVD_R$. An $AVD_R$ and a positive IVD ($AVD_L > AVD_R$) is illustrated in FIG. 1A. As can be appreciated from consideration of FIG. 1A, this pacing implementation produces pacing delivered first to the right ventricle and then to the left ventricle. An $AVD_R$ with a negative IVD ($AVD_L < AVD_R$) is illustrated in FIG. 1B. In this pacing implementation a pace is delivered to the left ventricle first followed by a pace to the right ventricle. In inhibited demand pacing, if an intrinsic right ventricular depolarization occurs during the $AVD_R$, then at least the scheduled right ventricular pacing is inhibited and possibly both RV and LV paces are inhibited. Correspondingly, if an intrinsic left ventricular depolarization occurs during the $AVD_L$, then at least the scheduled left ventricular pacing is inhibited.

One skilled in the art will recognize that CRT pacing described in terms of timing intervals $AVD_R$, $AVD_L$ may alternatively be described in terms of timing intervals $AVD_R$ and IVD, where $IVD=AVD_L-AVD_R$. For the purposes of the discussion herein, CRT pacing delays are described in terms of $AVD_R$ and $AVD_L$. This choice of terminology is made for purposes of explanation and does not impose any limitation upon the methods or devices described herein. Those skilled in the art will readily understand that the invention may alternatively be described and implemented using the terminology of $AVD_L$ and IVD or $AVD_R$ and IVD.

Methods, devices, and systems of the present invention provide for determination of the pacing delays implemented in CRT pacing therapy, such as the $AVD_R$ and/or $AVD_L$ used for cardiac resynchronization therapy. According to embodiments of the invention, adjustments made to one or more of the right and left ventricular pacing delays and right and left ventricular pacing energies are based on intrinsic conduction data and cardiac pacing response determination and also take into account heart rate. Embodiments of the invention are described in terms of CRT pacing involving biventricular pacing or LV only pacing, although the concepts apply as well to biatrial or four chamber pacing.

Figure 2:
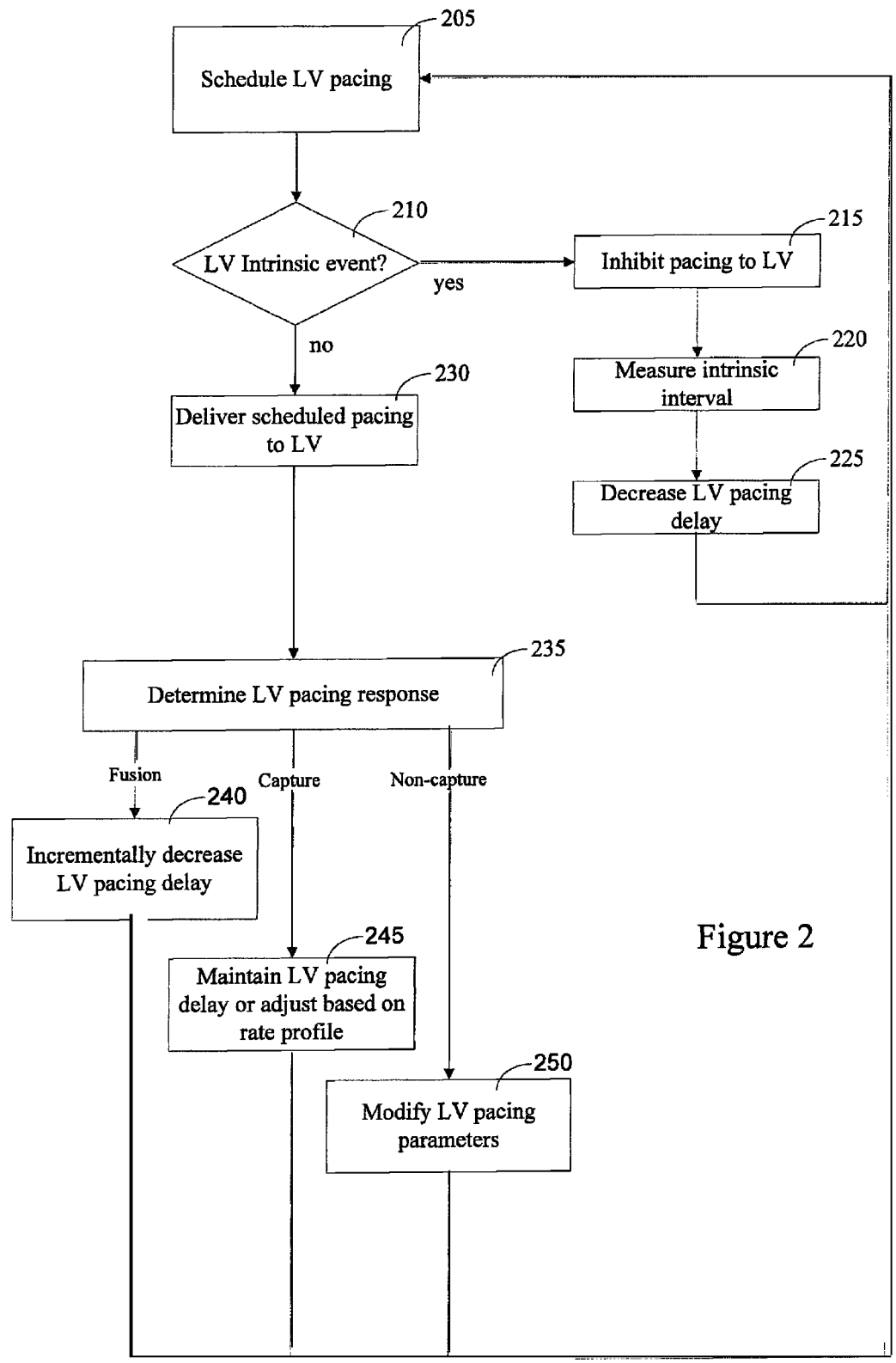
FIG. 2 is a flow diagram illustrating a process for adjusting CRT pacing delays based on LV capture status in accordance with embodiments of the invention.

The flow diagram of FIG. 2 illustrates a process for setting CRT pacing parameters in accordance with embodiments of the invention. In this example, cardiac resynchronization therapy (CRT) pacing that involves at least LV pacing is implemented along with beat by beat LV pacing response determination. An algorithm that determines the cardiac pacing response beat by beat is used to determine the responses of the LV or RV to the delivered paces. Pacing parameters including pacing delays and/or pacing energy are adjusted beat by beat based on the cardiac response to RV and LV pacing, or LV only pacing (e.g., capture, fusion, non-capture, etc.) and intrinsic interval measurements that indicate cardiac tissue conduction delays.

According to this process, CRT pacing including LV pacing is scheduled 205 for each cardiac cycle. As discussed in more detail above, CRT pacing includes scheduling the delivery of at least an LV pace relative to a pacing delay, denoted herein as the $AVD_L$. If an LV intrinsic event is sensed 210 during the $AVD_L$ and prior to delivery of the LV pace, pacing to the LV is inhibited 215 and the conduction interval between the atrial event and the intrinsic LV depolarization ($AVI_L$) is measured 220. The $AVD_L$ is decreased 225 based on the measured conduction interval. For example, the $AVD_L$ may be decreased by an amount being slightly greater than the difference between the current $AVI_L$ and the $AVD_L$. After decreasing the $AVD_L$ on the next cycle, LV capture is confirmed following delivery of the pacing pulse. If the LV pace is again inhibited on subsequent beats, the pacing delay may be decreased again until LV capture is detected.

If no intrinsic LV depolarization occurs 210 prior to expiration of the pacing delay, then LV pacing is delivered 230 as scheduled. Delivery of the LV pace may be followed by one of the four situations illustrated in FIG. 2. The LV may be captured by the pace, a fusion beat may result, or the LV pace may not produce capture. Non-capture of the LV may occur with or without an intrinsic depolarization during the cardiac cycle.

In some implementations, the cardiac pacing response of a ventricle may be determined by analyzing the morphology of the cardiac signal sensed following delivery of the pacing pulse. The sensed cardiac signal may be compared to templates or other types of references that characterize an expected morphology for various types of pacing responses. Morphology-based capture detection may be used to analyze peak amplitudes and/or peak timing of the cardiac signals within a capture detection window to determine if the features of he sensed cardiac signals are consistent with those expected for capture, fusion, or non-capture with intrinsic activation, for example. Non-capture without intrinsic activation may be determined if the cardiac signals do not surpass a threshold amplitude. Morphological analysis for cardiac response classification may be applied separately to the left and right ventricles based on the left and right cardiac signals sensed following pacing in the ventricles. In some scenarios, the cardiac signal analyzed for cardiac response determination may comprise the integral or the derivative of the sensed signal.

According to one morphology-based technique, the features of cardiac signal sensed following pacing are extracted. The extracted features are compared to template features characterizing a particular type of cardiac pacing response through the use of feature correlation coefficient analysis.

Some approaches for cardiac response determination are based on cancellation of depolarization wavefronts caused by paced or sensed cardiac events occurring in bilateral cardiac chambers, e.g., right and left ventricles. In one exemplary situation, after sequentially pacing both ventricles, the system senses for cardiac activity in the first-paced ventricle during a cross-chamber sensing window that follows the pacing pulse delivered to the second-paced ventricle. If both pacing pulses captured their respective chambers, the depolarization wavefront of the first-paced ventricle collides with a depolarization wavefront of the second-paced ventricle and cancels the cardiac activity in the first-paced ventricle during the cross chamber sensing window. If the first-paced ventricle was not captured, then no cancellation occurs, and cardiac activity responsive to the activation of the second paced chamber is evident in the cross chamber sensing window.

In various other implementations, capture verification may be achieved by analysis of hemodynamic changes, analysis of impedance, analysis of heart sounds and any other indicators of capture status.

In some embodiments, discrimination between capture, fusion, and non-capture with or without intrinsic activity may be achieved. For each of these response scenarios, the algorithm may implement a different process for adjusting pacing parameters. For example, detection of fusion is an indication that the pacing delay is slightly too long, and the $AVD_L$ may decreased 240 by an incremental amount to reduce the likelihood of fusion for subsequent beats. Non-capture with or without intrinsic activation may indicate insufficient LV pacing energy. If non-capture is detected, the algorithm implements 250 an increase in the LV pacing energy. If an intrinsic depolarization is detected along with the non-capture determination, then the $AVD_L$ may also be modified for the next cycle.

If LV capture is detected, the pacing energy is sufficient to achieve capture and no adjustments are made 245 to the LV pacing energy. The current $AVD_L$ is maintained for the next cardiac cycle. Optionally, as described in more detail below, the $AVD_L$ may be also adjusted to compensate for changes in the cardiac rate.

The flow diagram of FIG. 2 illustrates adjustment of LV pacing parameters, although adjustment of the RV pacing delay and/or pacing energy and/or adjustment of both the RV and LV pacing delays and/or pacing energies may be implemented in a same or similar manner. Table 1 provides a summary of pacing delay and/or pacing energy adjustments that may be made according to one embodiment.

TABLE 1

| Pacing response for current beat | | Basis for pacing parameter adjustments for next beat | | |
|---|---|---|---|---|
| RV | LV | $AVD_R$ | $AVD_L$ | LV Pacing energy |
| 1-1 C | S | no change | measured interval | no change |
| 1-2 C | C | no change | no change | no change |
| 1-3 C | NC, NC+I | no change | no change | increase by predetermined amount; schedule LV automatic threshold test |
| 1-4 C | F | no change | incremental | no change |
| 1-5 S | S | measured interval | measured interval | no change |
| 1-6 S | C | measured interval | no change | no change |
| 1-7 S | NC NC+I | measured interval | no change | increase by predetermined amount; schedule LV automatic threshold test |
| 1-8 S | F | measured interval | incremental | no change |
| 1-9 F | S | incremental | measured interval | no change |
| 1-10 F | C | incremental | no change | no change |
| 1-11 F | NC NC+I | incremental | no change | increase by predetermined amount; schedule LV threshold test |
| 1-12 F | F | incremental | incremental | |
| 1-13 NC | X | If RV loss of capture is detected, increase RV pacing energy by a predetermined amount and schedule RV automatic threshold test | | |

Table 1 illustrates 13 CRT pacing scenarios labeled 1-1 through 1-13 along with the basis for modification of pacing parameters for the next beat. During any cardiac cycle, one or both ventricles may intrinsically depolarize prior to a scheduled pace; a sensed ventricular depolarization is indicated by an S in Table 1. If the cardiac pace produces a propagating wave of depolarization, the pace may produce capture (C) of the ventricle or a fusion beat (F). If the ventricle is not captured by the pace, non-capture with or without intrinsic activation is detected. These non-capture possibilities are denoted NC+I and NC, respectively. In Table 1, an X denotes any possible pacing response, S, C, F, NC+I, and NC.

Consider, for example, scenario 1-1 listed in Table 1. In scenario 1-1, the RV pace of a cardiac cycle captures (C) the right ventricle. An intrinsic LV depolarization (S) is sensed prior to delivery of the LV pace. On the next cycle, the $AVD_R$ is maintained. The $AVD_L$ is adjusted based on the measured interval between the atrial event and the intrinsic left ventricular depolarization, $AVI_L$. In this example, the pacing energy of the RV pace and the LV pace remains unchanged because the RV pace produced capture, and because the LV intrinsically depolarized prior to delivery of an LV pace, providing no indication that the LV pacing energy is insufficient to produce capture.

Next, consider CRT pacing scenario 1-3 listed in Table 1. During a current cardiac cycle, the right ventricular pace produces capture (C) of the RV and the LV pace does not produce capture (NC) of the LV. Noncapture with intrinsic depolarization (NC+I) may be detected after delivery of the LV pace. On the next cardiac cycle, the RV pacing interval, $AVD_R$, is maintained. The LV pacing energy is increased by a predetermined amount. Optionally, the LV pacing interval, $AVD_L$, is adjusted based on the measured $AVI_L$, which is the interval measured between the atrial event and the intrinsic depolarization of the LV. An LV threshold test may be scheduled.

As a further example, consider CRT pacing scenario 1-4 listed in Table 1. During a current cardiac cycle, the RV pacing pulse produces capture (C) and a fusion beat (F) is detected following the LV pace. Thus, the LV pace appears to be of sufficient energy to produce capture, but the LV pace timing may be adjusted to decrease the likelihood of fusion. In this scenario, the $AVD_R$ remains unchanged and the $AVD_L$ is decreased by an incremental amount to reduce the likelihood of fusion occurring during the next cardiac cycle.

Table 1 illustrates other CRT pacing scenarios that may be interpreted in a similar manner to the examples provided above. In the example provided by Table 1, if loss of capture is detected for the RV, regardless of the LV response, RV pacing energy is increased and an RV threshold test is scheduled.

As previously discussed, CRT is delivered to improve a patient's cardiac pumping capability and is normally delivered in atrial tracking or AV sequential pacing modes. These pacing modes implement pacing delays such as $AVD_R$ and $AVD_L$ to improve synchronization of ventricular contractions. Optimally, the CRT pacing produces ventricular synchronization during systole after optimal pre-load by the atrial contractions. For optimal hemodynamics, it is desirable for the pacing delays to vary with atrial rate in a manner similar to the way the intrinsic AV interval normally varies with atrial rate to produce more physiologic pacing response. Variation in the pacing delays is especially desirable during elevated atrial rates which may be experienced more frequently by heart failure patients as the heart rate increases to compensate for the loss of pumping ability.

Variations in the $AVD_R$ and/or $AVD_L$ may be implemented based on the measured atrial rate which can be determined as the reciprocal of the interval between atrial sensed or paced beats. In one exemplary embodiment, rate-adjustments to the $AVD_R$ and/or $AVD_L$ are made for cardiac cycles that follow capture of the right and/or left ventricles, respectively and for cardiac cycles that follow non-capture of the right and/or left ventricles. The pacing delays for cardiac cycles subsequent to a cycle in which some intrinsic activation occurs, i.e., sensed ventricular depolarizations that inhibit ventricular pacing, fusion beats, or non-captured beats with intrinsic activation, are not varied according to rate but are adjusted based on the measured AV intervals ($AVI_R$ or $AVI_L$) of the previous cycle.

Figure 3A:
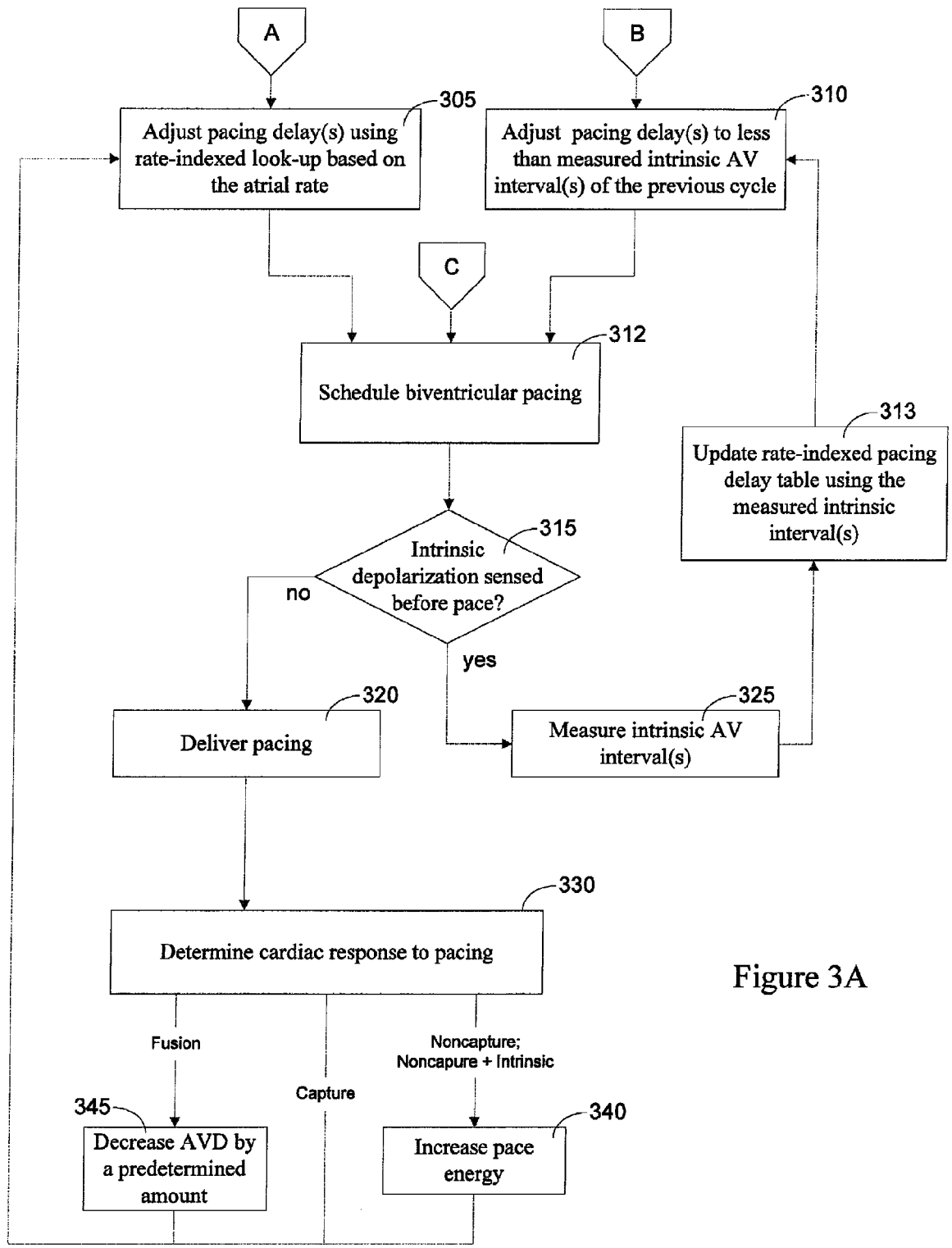
FIG. 3A is a flow diagram illustrating a process for adjusting CRT pacing delays based on capture status in conjunction with atrial rate in accordance with embodiments of the invention.

The flow diagram of FIG. 3A illustrates the concept of adjusting 305 the pacing delays $AVD_R$ and/or $AVD_L$ based on rate for cardiac cycles in which intrinsic ventricular depolarizations are absent and adjusting 310 the CRT pacing delays $AVD_R$ and/or $AVD_L$ based on measured intrinsic intervals of the previous cycle for cardiac cycles in which intrinsic ventricular depolarizations occur.

Whether one or more pacing delays $AVD_R$ and/or $AVD_L$ of a current cardiac cycle are adjusted for rate or are set to be less than measured intrinsic intervals $AVI_R$ and/or $AVI_L$ of the previous cardiac cycle is contingent on whether intrinsic depolarizations are sensed during the pacing delay(s) $AVD_R$ and/or $AVD_L$ during the previous cardiac cycle. If an intrinsic depolarization of a ventricle is sensed during a cardiac cycle before delivery of the pacing pulse to a ventricle, for example, then the associated intrinsic atrioventricular interval, $AVI_R$ and/or $AVI_L$, is measured 325 and the pacing delay(s), $AVD_R$ and/or $AVD_L$ used for the subsequent cardiac cycle are adjusted 310 to be less than the measured interval $AVI_R$ and/or $AVI_L$.

After CRT pacing delays $AVD_R$ and/or $AVD_L$ for a cardiac cycle are set 305, 310, CRT pacing is scheduled 312. If no intrinsic right or left ventricular depolarizations are sensed 315 during the $AVD_R$ and/or $AVD_L$ intervals, respectively, then the right and left ventricular pacing is delivered as scheduled. The cardiac response to pacing is determined 330. If the CRT pacing results in capture of a ventricle, the pacing delay for that ventricle during the next cardiac cycle is adjusted 305 according to atrial rate. If the CRT pacing did not result in capture for a ventricle, (i.e., non-capture or non-capture and an intrinsic beat, then the pacing energy for that ventricle is increased 340 and the pacing cycle for the next cardiac cycle is adjusted 305 according to atrial rate.

A fusion beat may occur following delivery of a pacing pulse. A fusion beat results when the depolarization wavefront initiated by the pace collides with an intrinsic depolarization wavefront very close to the pacing site. If the CRT pacing resulted in fusion of the right and/or left ventricles, the $AVD_R$ and/or $AVD_L$ are decreased 345 by a predetermined amount for the next cardiac cycle. The $AVD_R$ and/or $AVD_L$ may also be adjusted 305 according to atrial rate.

The measured intrinsic AV intervals, $AVI_R$ and/or $AVI_L$, which indicate AV conduction delays for right and left ventricles, respectively, may be used to update 313 a rate-indexed table of pacing delays. Calculation of pacing delays $AVD_R$ and/or $AVD_L$ based on measured intrinsic AV intervals ($AVI_R$ and/or $AVI_L$) and the development of a rate-indexed table of pacing delays based on measured intrinsic AV intervals is described in more detail below.

The rate-indexed look-up table (or equations) for determining pacing delays $AVD_R$ and/or $AVD_L$ may be initially determined and/or periodically updated based on clinical hemodynamic testing wherein the pacing delays are optimized for cardiac function for at various atrial rates. For example, cardiac function may be measured in terms of dP/dt, arterial pulse pressure, or measurements of cardiac output.

Clinical hemodynamic testing to determine optimal pacing delays at various atrial rates can be time consuming and difficult to accomplish. As an alternative or as a supplement to such clinical hemodynamic testing to determine optimal pacing delays, determination of optimal rate-based pacing delays may be based on measured intrinsic intervals which are collected by the implanted device. As described in connection with FIG. 3A, adjustment of the pacing delay for a ventricle based on heart rate may occur if pacing of the ventricle is not inhibited and no intrinsic depolarization of the ventricle occurs during the cardiac cycle. The algorithms described herein allow the device to achieve consistent capture of the RV and/or LV based on capture status during CRT pacing, while also making adjustments to account for atrial rate.

In some embodiments, pacing delays such as the $AVD_R$ and/or $AVD_L$ are adjusted beat by beat based on measured atrial rate, measured intrinsic intervals, and/or capture status of the previous beat. The pacing scenarios illustrated in Table 2 are similar to those previously discussed in connection with Table 1, except that the example of Table 2, the pacing delay adjustment is based on atrial rate for cardiac cycles in which no intrinsic depolarization is sensed.

TABLE 2

| Pacing response for current beat | | Basis for pacing parameter adjustments for next beat | | |
| --- | --- | --- | --- | --- |
| RV | LV | $AVD_R$ | $AVD_L$ | LV Pacing energy |
| 2-1 C | S | rate | measured interval | no change |
| 2-2 C | C | rate | rate | no change |
| 2-3 C | NC, NC + I | rate | rate | increase; schedule LV threshold test |
| 2-4 C | F | rate | incremental | no change |
| 2-5 S | S | measured interval | measured interval | no change |
| 2-6 S | C | measured interval | rate | no change |
| 2-7 S | NC, NC + I | measured interval | rate | increase; schedule LV threshold test |
| 2-8 S | F | measured interval | incremental | no change |
| 2-9 F | S | incremental | measured interval | no change |
| 2-10 F | C | incremental | rate | no change |
| 2-11 F | NC, NC + I | incremental | rate | increase; schedule LV threshold test |
| 2-12 F | F | incremental | incremental | no change |
| 2-13 NC, NC + II | X | If RV loss of capture is detected, increase RV pacing energy and perform RV automatic threshold test | | |

In pacing cycle scenario 2-1, for example, the RV pace captures the right ventricle and an intrinsic LV depolarization occurs prior to delivery of the LV pace. On the next cycle, the $AVD_R$ is adjusted to compensate for an increase or decrease in cardiac rate. The $AVD_L$ is adjusted based on $AVI_L$, which is the intrinsic AV interval measured between the atrial event and the intrinsic LV depolarization of the previous cardiac cycle. In this example, the pacing energy of the LV pace remains unchanged because there is no indication that the LV pacing energy is insufficient to produce capture.

Next, consider CRT pacing scenario 2-3. During a cardiac cycle, the right ventricular pace produces capture of the RV and the LV pace does not produce capture of the LV, but an intrinsic LV depolarization is detected after delivery of the LV pace. On the next cardiac cycle, the RV pacing interval, $AVD_R$, is adjusted to compensate for any changes in rate. The LV pacing energy is increased by a predetermined amount and an LV capture threshold test may be scheduled. The LV pacing interval, $AVD_L$, is adjusted based on the intrinsic interval $AVI_L$.

Finally, consider CRT pacing scenario 2-4. During a cardiac cycle, the RV pacing pulse produces capture and a fusion beat is detected following the LV pace. Thus, the LV pace appears to be of sufficient energy to produce capture, but the pacing timing may be adjusted to decrease the likelihood of fusion. In this scenario, the RV pacing delay $AVD_R$ may be adjusted to compensate for changes in rate and the LV pacing delay $AVD_L$ may be adjusted by an incremental decrease to reduce the likelihood of fusion occurring during the next cardiac cycle.

After detection of an intrinsic depolarization, the pacing delay (AVD) for the next cardiac cycle is decreased to be less than the measured intrinsic AVI of the previous cycle. In some embodiments, during subsequent cycles, the pacing delay is gradually increased until it matches the pacing delay indicated by the rate-indexed look-up table.

Figure 3B:
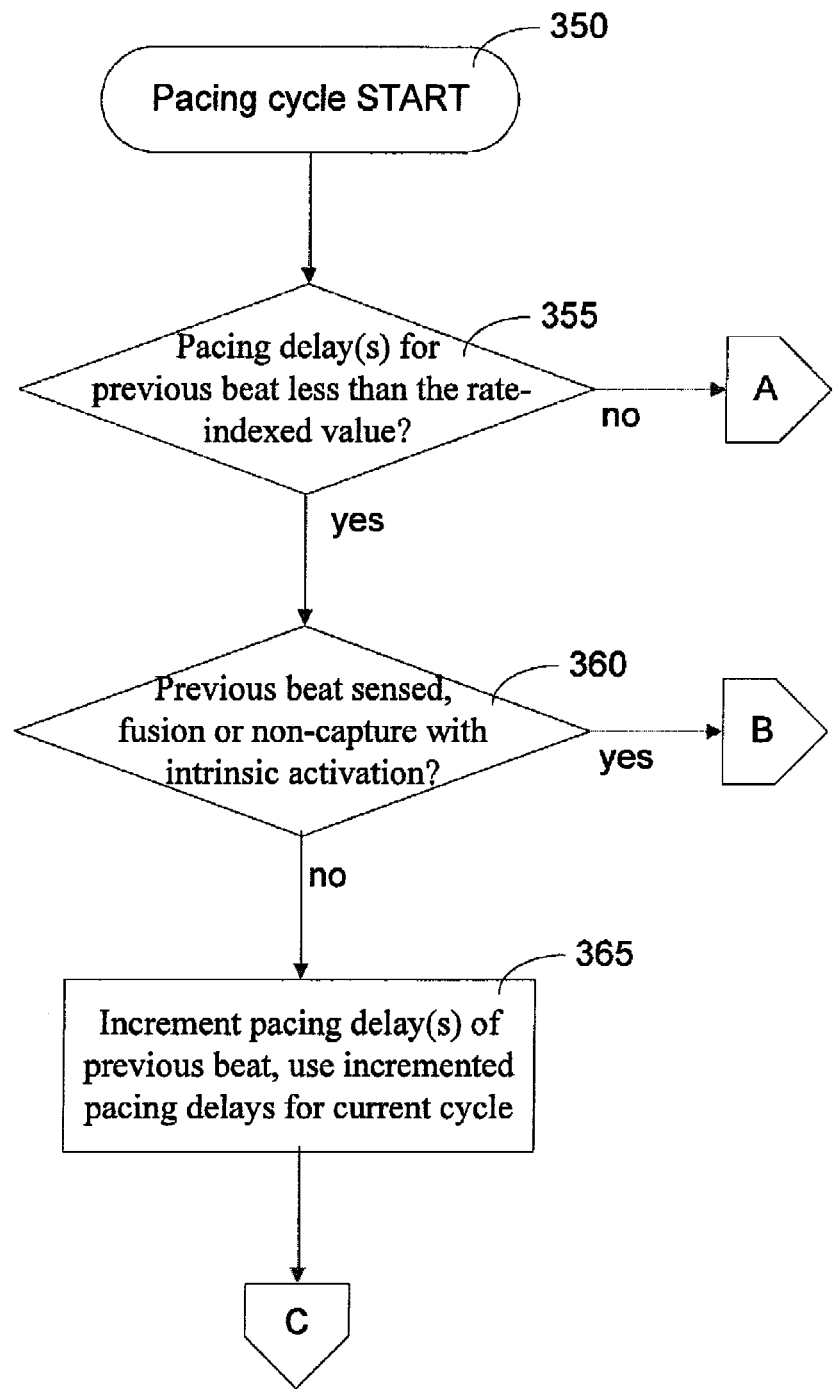
FIG. 3B illustrates a process of decreasing a pacing delay following a sensed beat and then gradually lengthening the pacing delay during subsequent beats to promote consistent LV pacing in accordance with embodiments of the invention.

Gradual increase in a pacing delay is illustrated by the flow diagram of FIG. 3B. At the start of a pacing cycle 350, the device determines if the pacing delay $AVD_R$ and/or $AVD_L$ used for the immediately previous cycle was less than 355 the rate-indexed look up table value for the previous cycle. If the pacing delay $AVD_R$ and/or $AVD_L$ was not less than 355 the rate-indexed value, then the pacing delay $AVD_R$ and/or $AVD_L$ for the current cycle is determined 305 (FIG. 3A) based on atrial rate. If the pacing delay $AVD_R$ and/or $AVD_L$ for the immediately previous cycle was less than 355 the rate-indexed value, then the pacing delay $AVD_R$ and/or $AVD_L$ has been shortened in response to an intrinsic depolarization that occurred during a prior cycle. The device determines 360 if the immediately previous cycle included an intrinsic depolarization (pace inhibited by a sensed depolarization, fusion or non-capture with intrinsic activation) by analyzing the pacing delay $AVD_R$ and/or $AVD_L$. If the pacing delay $AVD_R$ and/or $AVD_L$ has been recently decreased, then the pacing delay that was used for the immediately previous cycle is incrementally increased 365 and CRT pacing is scheduled 312 (FIG. 3A). If the immediately previous cycle included 360 an intrinsic depolarization, then the pacing delay $AVD_R$ and/or $AVD_L$ for the next beat is decreased 310 (FIG. 3A) to a value less than the measured intrinsic interval $AVI_R$ and/or $AVI_L$. Incremental increases are made to pacing delays $AVD_R$ and/or $AVD_L$ of subsequent cycles, so long as no intrinsic depolarizations occur, until the rate-indexed value is achieved.

The rate-based adjustments described herein may be made using rate-indexed intrinsic interval data collected by the device over time. Appropriate adjustments to the pacing delays may be stored in a look-up table indexed by rate and/or expressed as a function of rate or expressed as a series of rate-indexed functions. One example of methods and systems for implementation of rate-based adjustment of pacing intervals is described in commonly owned U.S. Pat. No. 7,123,960 which is incorporated herein by reference.

CRT is used to control the conduction sequence of ventricular contractions by applying ventricular paces to compensate for conduction defects between and/or within the ventricles. For example, CRT is particularly useful to treat left ventricular dysfunction which arises when portions of the left ventricle contracts later than normal during an intrinsic cardiac cycle. CRT pacing involving biventricular pacing or left ventricle-only pacing compensates for the later than normal contraction by pre-exciting the left ventricle with a first pace delivered to the left ventricle followed by a right ventricular pace (or intrinsic depolarization).

The left ventricular pace excites the left ventricular free wall while the right ventricular pace excites the ventricular septum. The desired situation is simultaneous contraction of the left ventricular free wall and septum (septum-free wall fusion). When clinical hemodynamic testing is performed on a population of subjects to determine the optimal values of the pacing delays, there is found to be a correlation between the optimal delays for a particular subject and that subject's measured right and left atrioventricular intervals, $AVI_R$ and $AVI_L$, respectively, during an intrinsic beat. As described more fully in U.S. Pat. No. 7,123,960, the optimum pacing delays for a particular patient may be estimated from intrinsic conduction data in terms of specified coefficients as:

$$AVD_R = k_5 AVI_R + k_6 AVI_L + k_7 \quad [1]$$

and $$AVD_L = k_8 AVI_R + k_9 AVI_L + k_{10} \quad [2]$$

In order determine the specified coefficients, $k_5$ through $k_{10}$, clinical population data is obtained that relates particular values of the measured intrinsic conduction parameters to an optimum value of the pre-excitation timing parameter as determined by concurrent measurement of another parameter reflective of cardiac function (e.g., maximum dP/dt or minimum atrial rate). A linear regression analysis is then performed to derive values of the specified coefficients used in the formula for setting the pacing delays, the specified coefficients thus being regression coefficients.

CRT pacing parameters that are adjusted for rate may be achieved by storing a set of rate-indexed equations for $AVD_R$ and/or $AVD_L$, or by storing a look-up table of values which are calculated from these equations or otherwise determined. These rate-based pacing delays may be used for pacing delay adjustment as described above for certain pacing cycles.

In an exemplary embodiment, the system computes the rate adjusted $AVD_R$ and/or $AVD_L$ intervals to be used for delivering CRT by collecting intrinsic conduction data at different atrial rates. The atrial rate may vary intrinsically or as the result of variations in pacing. The intervals $AVI_R$ and/or $AVI_L$, are measured for various rates and these intrinsic $AVI_R$ and/or $AVI_L$ intervals are used to calculate, e.g., via the equations such as [1] and [2] above, pacing delays which are stored in a rate-indexed look up table. For example, each measured $AVI_R$ and/or $AVI_L$ may be averaged or otherwise combined with previously measured $AVI_R$ and/or $AVI_L$ intervals, respectively. The average or combination of these intrinsic intervals are used to calculate or re-calculate rate-indexed pacing delays. In some embodiments, the rate-indexed pacing delays $AVD_R$ and/or $AVD_L$ are stored as entries in a look up table. The rate-indexed look-up table entries may be used to implement rate-based adjustment of CRT pacing delays for subsequent cardiac cycles. The pacing delays used for CRT pacing may use the look up table entries and additional adjustments to the look up table values may be made beat by beat based on whether an intrinsic depolarization occurred and/or on the capture status of a previous cycle.

After development of a look up table based on measured intrinsic intervals for at least two atrial rates, the implantable device may vary the pacing delays as the atrial rate changes. One look up table entry may correspond to a range of atrial rates. If there is no pacing delay value corresponding to a particular rate, the device may interpolate between pacing delay values for atrial rates above and below the present rate to determine the rate adjusted pacing delay.

In some embodiments, rate-based pacing delays may be determined by analyzing stored data related to the cardiac pacing response status (capture, non-capture, fusion, etc.) of previous cycles. From this analysis, pacing delays that produce superior capture performance for each atrial rate can be stored for later use. According to this approach, the implantable cardiac device measures and stores in memory the atrial rate, pacing delays, measured intrinsic intervals, and the response to pacing for a number of cardiac cycles. The stored information can be analyzed by the implantable device, a patient-external device, or by a human analyst to determine appropriate rate-based pacing delays that produce consistent capture during CRT pacing.

For example, if the stored data reveals that a particular pacing delay or pacing delay range used at a particular rate or rate range fails to produce consistent CRT pacing, then the pacing delay for the rate or rate range may be decreased so that consistent biventricular or LV pacing is promoted. The analysis may be performed, for example, by comparing, at each rate range of interest, the percentage or number of paced beats for each ventricular chamber to the percentage or number of beats in which intrinsic ventricular depolarizations inhibited ventricular pacing in the chamber. The analysis may also take into account the percentage or number of paced beats that resulted in capture, non-capture, non-capture with intrinsic depolarization and/or fusion.

Processes for analyzing the stored data, computing pacing delays, and/or programming the implantable device with rate-indexed pacing delays may be implemented by an external device, may be implemented by an implanted device, or both devices may be used to implement the procedure. Furthermore, these processes may be performed in fully automatic or semi-automatic modes. For example, operating in an automatic mode, the implantable device and the external device communicate via a telemetry link. The external device receives from the implantable device data such as electrogram signals, markers corresponding to sensed events, measured intervals indexed by rate, cardiac pacing response information, and/or other data. The external device processes the information acquired from the implantable device to determine rate-indexed $AVD_R$ and/or $AVD_L$ pacing delays and programs the implantable device with a rate-indexed look up table of pacing delays.

In another example of an automatic mode, the implantable device operates independently and automatically, analyzing electrogram data, measured intervals, and pacing response status to determine the rate-indexed pacing delays and programs the rate-indexed table of pacing delays for use in subsequent cycles.

Operating in a semi-automatic mode, the external device (e.g., external programmer) or implantable device may provide for display of textual and/or graphical data and analyses, histograms, statistical analysis in an appropriate format for viewing by a clinical user. For example, the external device may analyze the measured intrinsic intervals, the cardiac pacing responses, and the cardiac rate data and present the analysis to the user via a user interface of the external device. The external device may present graphs indicating relationships between various cardiac pacing responses and cardiac rate, for example. This information can be presented via a display on the external device to assist the physician in selecting appropriate pacing delays that will achieve consistent CRT pacing. The user interface may be arranged to accept inputs from the human analyst which cause the implantable device to be programmed with selected pacing delays. For example, in some semi-automatic modes, the external device includes a user interface configured to generate a display of textual and/or graphical information and to receive commands from a user, e.g., via a touch screen, keyboard, mouse, or other input device.

The external device and/or implantable device may determine recommended pacing delays which are presented to the human analyst via the display. A user may accept pacing delay recommendations made by the device, or may override these recommendations and select different pacing delays which are then programmed into the implantable device.

Figure 4A:
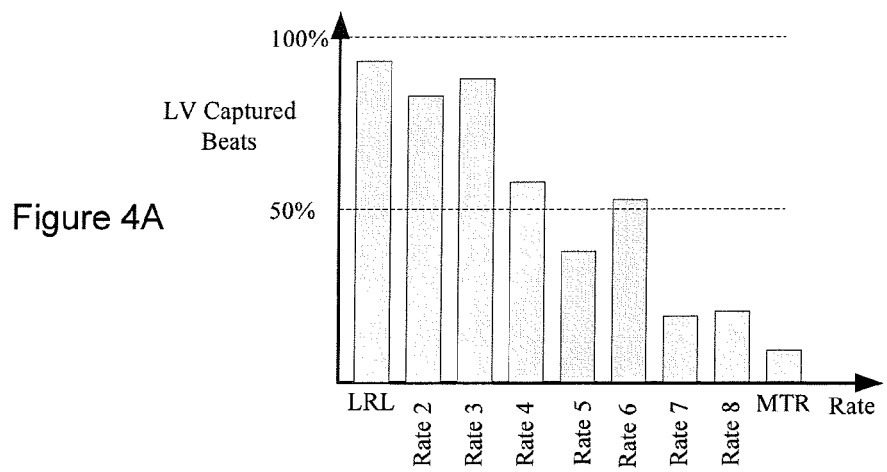
FIGS. 4A-4C, and 5 illustrate bar graphs summarizing stored information related to various cardiac responses during pacing which may be displayed to facilitate determination of CRT pacing delays in accordance with embodiments of the invention.
Figure 4B:
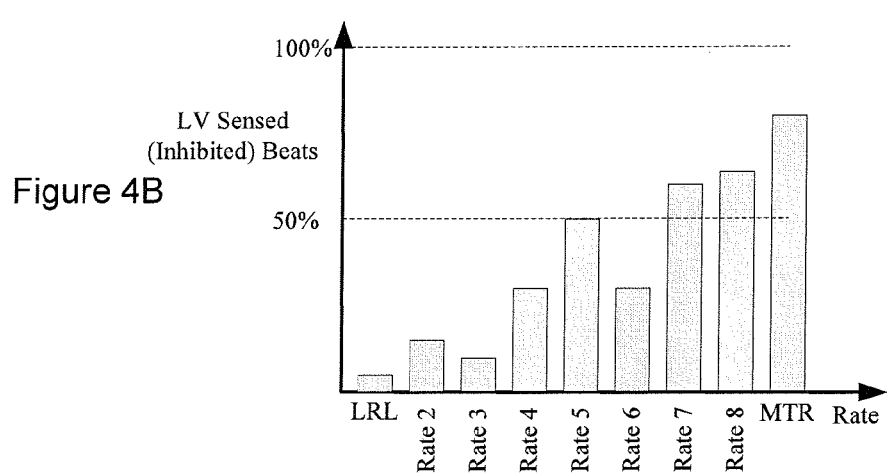
Figure 4C:
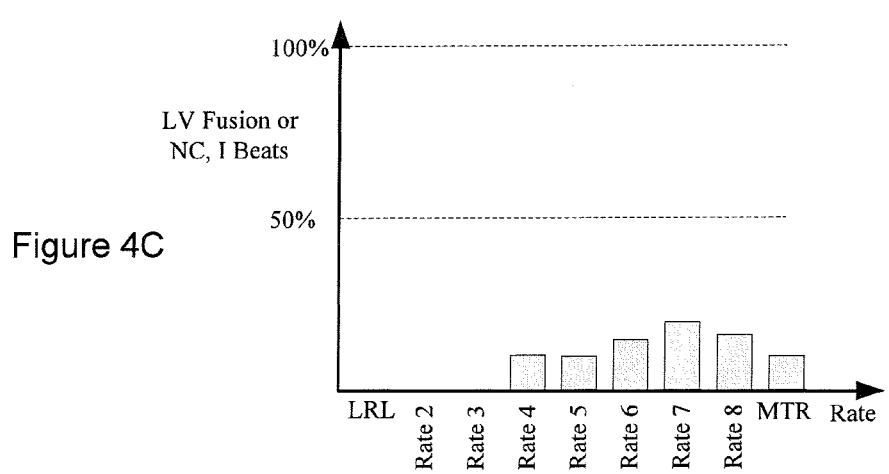

FIGS. 4A-C provide an illustrative example of a data analysis for LV beats in 9 atrial rate ranges between and including the device's lower rate limit (LRL) and the maximum tracking rate (MTR). FIGS. 4A-C illustrate graphs that may be generated on a display for viewing by a human analyst to allow the analyst to review device performance or to select rate-indexed pacing delays. Each of these graphs provides the percentage of certain types of LV cycles for the 9 rate ranges. Similar graphs may be generated for RV cycles, however, for simplicity, only LV cycles are described in this example.

FIG. 4A provides the percentage of captured LV cycles for 9 rate ranges. FIG. 4B illustrates the number of LV cycles in which a sensed intrinsic LV depolarization inhibited the scheduled LV pace. FIG. 4C illustrates the number of paced LV cycles that included a fusion beat or non-capture with intrinsic activation. The number of LV cycles that resulted in non-capture without intrinsic activation may also be displayed, but this graph is not shown in this particular example.

Figure 5:
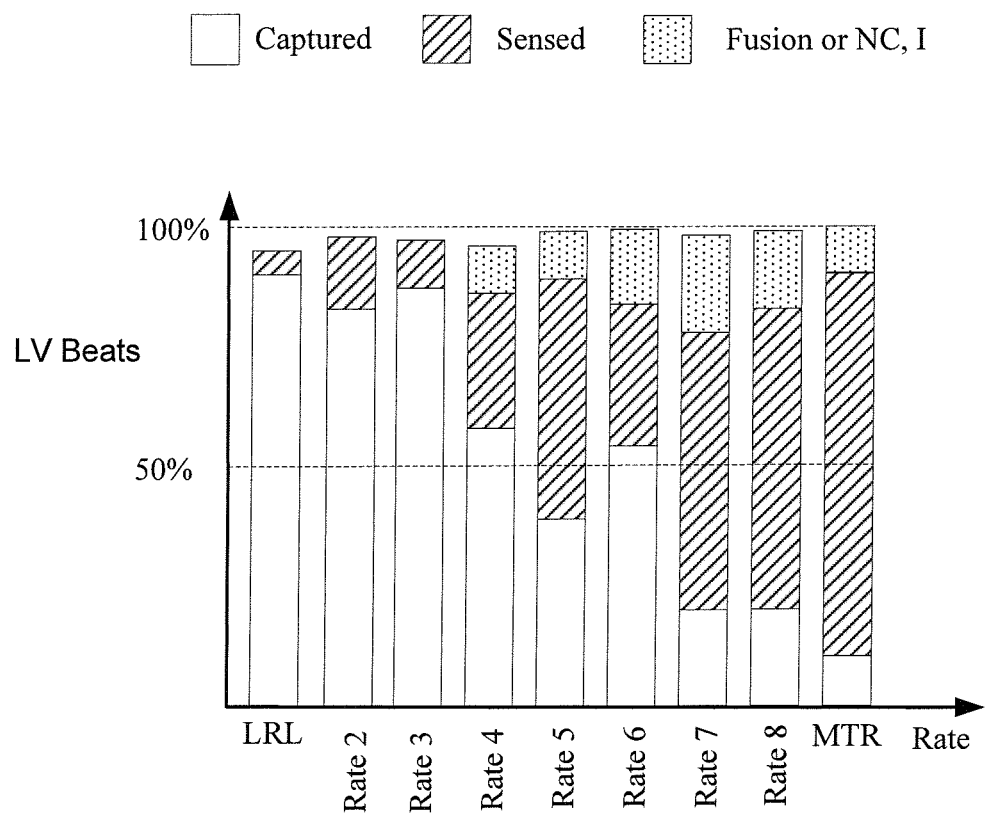

FIG. 5 illustrates an alternate graph comprising a stacked bar graph that may be used to display multiple types of pacing cycles on the same set of axes.

The implantable device and/or the external device may take certain actions as a result of changes in the percentage of captured beats achieved by the CRT pacing. For example, if the percentage of captured beats for the LV and/or RV in one or more rate ranges falls below a programmable threshold percentage, an alert may be generated and sent to the clinician. Alternatively, the programmable threshold may be automatically reprogrammed by the device with a notification of the change sent to the clinician. The device may be configured to allow any level or frequency of notification and/or automaticity with regard to reprogramming device parameters as desired.

The device may analyze stored data and select pacing delays to achieve improved device performance with the goal of achieving a higher number of captured beats. A format for displaying recommended optimized pacing delays which have been selected by the device is illustrated in FIG. 6, although alternate formats may be used. In FIG. 6, the recommended optimized $AVD_L$ 605 is illustrated for each rate 610. As further illustrated in FIG. 6, the previous $AVD_L$ 615 used for each rate and measured $AVI_L$ 625 and measured $AVI_R$ 630 for each rate may also be displayed to the user for comparison.

In some embodiments, the human analyst may accept or reject the pacing delays recommended by the device for each rate and/or may substitute alternate pacing delays. For example, in some implementations, the analyst may independently modify the recommended pacing delays for each rate by operating scroll bars 620.

After the pacing delays for each rate have been selected, the device may perform a simulation and display the results of the simulation to the user. The simulation results may be displayed as bar graphs or stacked bar graphs similar to the graphs of FIGS. 5A and 5B, for example. After viewing the results of the simulation, if the user is satisfied with the selected pacing delays, the user may confirm the selections, causing the pacing delay selections to be uploaded to the implantable device.

A wide variety of cardiac devices may be configured to implement determination of pacing parameters in accordance with the present invention. A non-limiting, representative list of such devices includes cardiac monitors, pacemakers, cardioverters, defibrillators, resynchronizers, and other cardiac monitoring and therapy delivery devices. These devices may be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes).

Figure 7:
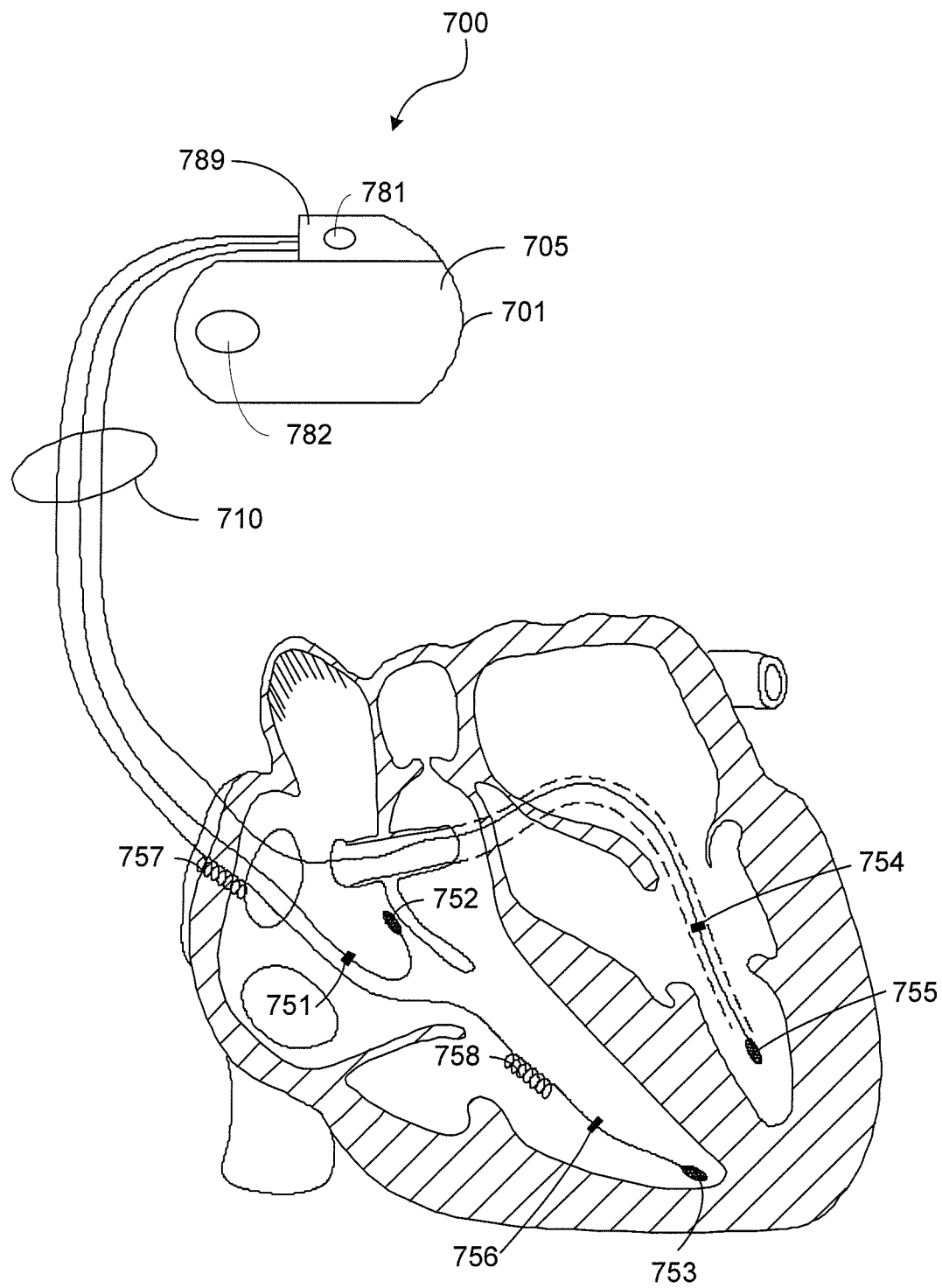
FIG. 7 is a view of an implantable cardiac device that may be used for CRT pacing using pacing delays determined in accordance with embodiments of the invention.

FIG. 7 illustrates a patient-implantable medical device (PIMD) that may be used for CRT pacing in accordance with embodiments of the invention. In this example, the implantable device 700 includes an implantable pulse generator 705 electrically and physically coupled to an intracardiac lead system 710.

Portions of the intracardiac lead system 710 are inserted into the patient's heart. The intracardiac lead system 710 includes electrodes 751-758 configured to sense electrical cardiac activity of the heart and deliver electrical stimulation to the heart. Additionally, the cardiac electrodes 751-758 and/or other sensors may be used to sense the patient's transsthoracic impedance, and/or sense other physiological parameters, such as cardiac chamber pressure or temperature.

The electrodes 751-758 shown in FIG. 7 illustrate one possible electrode arrangement. Many other electrode arrangements, including intracardiac and/or subcutaneous intrathoracic and non-intrathoracic electrodes, may be used and are considered to fall within the scope of the invention. The lead system 710 may include wired and/or wirelessly coupled electrodes and/or sensors. In wireless configurations, sensed signals from these electrodes and/or sensors are wirelessly communicated to the PIMD and/or may be wirelessly coupled to a patient-external device.

Portions of the housing 701 of the pulse generator 705 may optionally serve as one or multiple can or indifferent electrodes. The housing 701 is illustrated as incorporating a header 789 that may be configured to facilitate removable attachment between one or more leads and the housing 701. The housing 701 of the PIMD may include one or more can electrodes 782. The header 789 of the PIMD may include one or more indifferent electrodes 781.

Communications circuitry is disposed within the housing 701 for facilitating communication between the pulse generator 705 and a patient-external device, such as an external programmer or advanced patient management (APM) system, for example. The communications circuitry may also facilitate unidirectional or bidirectional communication with one or more implanted, external, cutaneous, or subcutaneous physiologic or non-physiologic sensors, patient-input devices and/or information systems.

The pulse generator 705 may optionally incorporate sensors which are used to sense patient activity as well as various respiratory and cardiac related conditions. For example, sensors may be optionally configured to sense respiration, snoring, activity level, chest wall movements, rales, coughing, heart sounds, murmurs, and other information. The patient activity information may be used in combination with rate information for optimal setting of device timings.

For example, the lead system 710 and pulse generator 705 of the CRM 700 may operate to provide one or more transthoracic impedance sensors and circuitry capable of acquiring the patient's respiratory waveform and deriving respiration-related information. The transthoracic impedance sensor may include, for example, one or more intracardiac electrodes 751-758 positioned in one or more chambers of the heart. The intracardiac electrodes 751-758 may be coupled to impedance drive/sense circuitry positioned within the housing 701 of the pulse generator 705. Information from the transthoracic impedance sensor and/or an activity sensor may be used to adapt the rate of pacing to correspond to the patient's activity and/or hemodynamic need.

The lead system 710 may include one or more cardiac pace/sense electrodes 751-756 positioned in, on, or about one or more heart chambers for sensing electrical signals from the patient's heart and/or delivering pacing pulses to the heart. The intracardiac sense/pace electrodes 751-756, such as those illustrated in FIG. 7, may be used to sense and/or pace one or more chambers of the heart, including the left ventricle, the right ventricle, and/or the right atrium. In some embodiments, electrodes may be also provided for pacing the left atrium. The lead system 710 may include one or more defibrillation/cardioversion electrodes 757, 758 for delivering defibrillation/cardioversion shocks to the heart.

In some embodiments, the pulse generator 705 includes circuitry for detecting cardiac tachyarrhythmias and/or for controlling anti-tachyarrhythmia pacing, cardioversion and/or defibrillation therapy in the form of electrical stimulation pulses or shocks delivered to the heart through the electrodes of the lead system 710 and/or the housing electrodes 781, 782.

In addition to controlling the therapy operations described above, the pulse generator 705 includes circuitry for implementing rate-indexed pacing delays for CRT pacing as described herein, including measuring cardiac rate, measuring intrinsic intervals, determining the response to pacing, storing a look-up table with optimized pacing parameters and/or for determining one or more pacing parameters, such as $AVD_L$, $AVD_R$ for CRT pacing.

In some embodiments, the pulse generator 705 may be configured to transfer sensed or derived information relevant to pacing parameter determination to a patient-external device. Following download of the implantably sensed or derived information, the pacing parameter determination may be made automatically or semi-automatically by the patient-external device with or without interaction with a human analyst. Following determination of the pacing delays, the information can be uploaded to the pulse generator 705 and subsequently used to control the timing of pacing pulses delivered to the heart in such a way that promotes LV capture and improves cardiac function.

Figure 8:
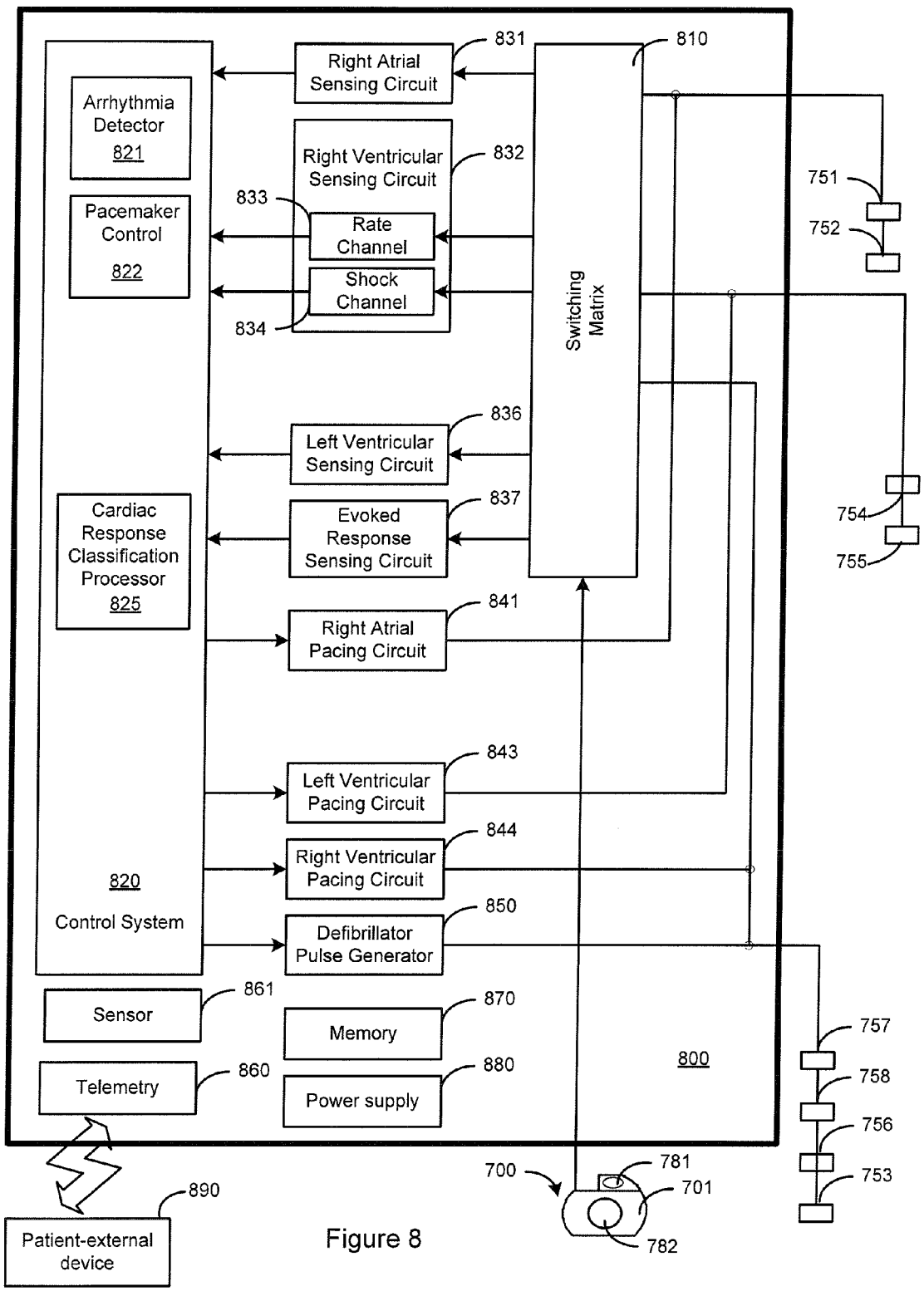
FIG. 8 is a block diagram of a cardiac system capable of utilizing cardiac pacing response status and rate information to adjust pacing delays for consistent LV pacing in accordance with embodiments of the invention.

FIG. 8 is a block diagram of a cardiac therapy system that may be employed to provide CRT pacing using pacing delays selected to promote consistent LV capture in accordance with embodiments of the invention. The various components of the system illustrated in FIG. 8 cooperate to perform algorithms that achieve pacing therapy operations as described, for example, by the flow diagrams of FIGS. 2, 3A, and 3B.

The cardiac system illustrated in FIG. 8 includes an external programmer 890 and the pulse generator 700 having circuitry 800 enclosed within an implantable housing 701. The cardiac system also includes a lead system deploying various electrodes 751-758 which are electrically coupled to the pulse generator circuitry 800. The pulse generator circuitry 800 includes circuitry for receiving cardiac signals sensed via the cardiac electrodes and delivering electrical stimulation energy to the heart in the form of pacing pulses or defibrillation shocks. The circuitry 800 of the pulse generator 700 is encased and hermetically sealed in a housing 701 suitable for implanting in a human body. Power to the pulse generator circuitry 800 is supplied by an electrochemical battery 880. A connector block (not shown) is attached to the housing 701 of the pulse generator 700 to allow for the physical and electrical attachment of the lead system conductors to the pulse generator 700.

The pulse generator circuitry 800 may comprise a programmable microprocessor-based system, including a control system 820 and a memory 870. The memory 870 can be used to store parameters for various pacing, defibrillation, and sensing operations, along with other information for controlling therapy delivery. The memory 870 is capable of storing a rate-indexed look up table that includes pacing delay values $AVD_L$, $AVD_R$. The memory may also store electrogram signal data, marker information, measured cardiac rates and intrinsic intervals, e.g., $AVI_L$, $AVI_R$, and/or cardiac data. The stored data may be obtained from long-term patient monitoring which may be used for determining patient condition trends and/or for other diagnostic purposes. Data stored in the memory 870 may be transmitted to a patient-external device 890, such as a programmer unit or advanced pacing management server as needed or desired.

The control system 820 and memory 870 may cooperate with other components of the pulse generator circuitry 800 to implement sensing and therapy operations of the cardiac system. The control system 820 includes a cardiac response classification processor 825 that has the capability to discriminate between various pacing responses, for example, capture, fusion, non-capture, and non-capture with intrinsic activation. The control system 820 also includes additional functional components, including a pacemaker control circuit 822 which includes timing circuitry for controlling CRT pacing using $AVD_L$ and $AVD_R$ pacing delays. The pulse generator circuitry 800 may also include an arrhythmia detector 821 and circuitry 850 for delivering defibrillation and/or cardioversion therapy to terminate detected tachyarrhythmias.

Telemetry circuitry 860 may be implemented to provide communications between the pulse generator circuitry 800 and the patient-external device 890. In one embodiment, the telemetry circuitry 860 and the programmer unit 890 communicate using a wire loop antenna and a radio frequency telemetric link to receive and transmit signals and data between the external unit 890 and the telemetry circuitry 860. In this manner, programming commands and other information may be transferred between the control system 820 and the external device 890.

The patient-external device 890 may be an external programmer or advanced patient management (APM) system. The advanced patient management system allows physicians or other personnel to remotely and automatically monitor cardiac and/or other patient conditions. Via an APM system, a physician may remotely alter therapy parameters, perform device and/or patient diagnostic testing, and/or access information stored in the implantable device. In one example, a cardiac pacemaker/defibrillator, or other device, may be equipped with various telecommunications and information technologies that enable real-time data collection, diagnosis, and treatment of the patient via an APM system.

In the embodiment illustrated in FIG. 8, electrodes RA-tip 752, RA-ring 751, RV-tip 753, RV-ring 756, RV-coil 758, SVC-coil 757, LV distal electrode 755, LV proximal electrode 754, indifferent electrode 781, and can electrode 782 are coupled through a switch matrix 810 to sensing circuits 831-837.

A right atrial sensing circuit 831 serves to detect and amplify electrical signals from the right atrium of the heart. Bipolar sensing in the right atrium may be implemented, for example, by sensing voltages developed between the RA-tip 752 and the RA-ring 751. Unipolar sensing may be implemented, for example, by sensing voltages developed between the RA-tip 752 and the can electrode 782. Outputs from the right atrial sensing circuit 831 are coupled to the control system 820 where sensed atrial depolarization may be utilized to implement atrial tracking pacing modes, for example.

A right ventricular sensing circuit 832 serves to detect and amplify electrical signals from the right ventricle of the heart. The right ventricular sensing circuit 832 may include, for example, right ventricular rate channel sensing circuitry 833 and right ventricular shock channel sensing circuitry 834. Right ventricular cardiac signals sensed through use of the RV-tip 753 electrode are right ventricular near-field signals, and are denoted rate channel signals. A bipolar RV signal may be sensed as a voltage developed between the RV-tip 753 and the RV-ring 756. Alternatively, bipolar sensing in the right ventricle may be implemented using the RV-tip electrode 753 and the RV-coil 758. Unipolar sensing in the right ventricle may be implemented, for example, by sensing voltages developed between the RV-tip 753 and the can electrode 782.

Right ventricular cardiac signals sensed through use of the defibrillation electrodes are far-field signals and are denote shock channel signals. More particularly, a right ventricular shock channel signal may be detected as a voltage developed between the RV-coil 758 and the SVC-coil 757. A right ventricular shock channel signal may also be detected as a voltage developed between the RV-coil 758 and the can electrode 782. In another configuration the can electrode 782 and the SVC-coil electrode 757 may be electrically shorted and a RV shock channel signal may be detected as the voltage developed between the RV-coil 758 and the can electrode 782/SVC-coil 757 combination.

Some embodiments may include circuitry and electrodes for sensing left atrial signals. In these embodiments, electrodes are electrically coupled to the left atrium and the pulse generator circuitry 800 includes a left atrial sensing circuit which serves to detect and amplify electrical signals from the left atrium of the heart.

Optionally, an LV coil electrode (not shown) may be inserted into the patient's cardiac vasculature, e.g., the coronary sinus, adjacent the left heart. Signals detected using combinations of the LV electrodes, 755, 754, LV coil electrode (not shown), and/or can electrode 782 may be sensed and amplified by the left ventricular sensing circuitry 836.

Various combinations of the electrodes 771-758, 781 and 782 may be utilized in connection with pacing the heart. The pacemaker control circuit 822, in combination with pacing circuitry for the right atrium 841, left ventricle 843, and right ventricle 844 generates pacing pulses which are delivered via electrode combinations selected from electrodes 751-758, 781 and 782. The pacing electrode combinations may be used to effect bipolar or unipolar pacing pulses to a heart chamber using one of the pacing vectors as described above.

The switching matrix 810 may be operated to couple selected combinations of electrodes 751-758, 781 and 782 to the sensing circuits 831-835, the pacing and defibrillation circuits 841, 843, 844, 850 and/or an evoked response sensing circuit 837. The evoked response sensing circuit 837 serves to sense and amplify signals developed using selected combinations of electrodes to discriminate between the various responses to pacing in accordance with embodiments of the invention. The evoked response sensing circuit 837 is coupled to the cardiac response classification processor 825 which analyzes the output of the evoked response sensing circuit 837 to classify the cardiac pacing response. The cardiac signal sensed following delivery of a pacing pulse may be analyzed to identify the response to pacing as left chamber capture only, right chamber capture only, multi-chamber capture, fusion, non-capture, or non-capture with intrinsic activation, for example.

In some implementations, the pulse generator circuitry 800 may include a sensor 861 that is used to sense the patient's activity or hemodynamic need. In one implementation, the sensor may comprise, for example, an accelerometer configured to sense patient activity. In another implementation, the sensor 861 may comprise an impedance sensor configured to sense patient respiration. The output of the sensor indicates the patient's activity and/or hemodynamic requirements and may be used to determine a sensor-indicated pacing rate. The pacing output of the pulse generator 700 may be adapted based on the sensor-indicated pacing rate signal to provide rate-adaptive pacing.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A cardiac therapy system capable of delivering cardiac resynchronization therapy (CRT) that includes pacing at least the left ventricle, the system comprising:
   electrodes configured to electrically couple to right and left ventricles;

sensing circuitry configured to sense cardiac signals via the electrodes, the cardiac signals including intrinsic depolarization signals;

pacing circuitry configured to generate pacing pulses deliverable through the electrodes;

cardiac response classification circuitry configured to determine cardiac responses to the pacing pulses; and pacing control circuitry configured to control the pacing circuitry, the pacing control circuitry configured to schedule delivery of CRT pacing to at least one ventricle relative to a pacing delay for the ventricle during a cardiac cycle, and, if an intrinsic depolarization is detected during the pacing delay, to inhibit the scheduled CRT pacing to the ventricle, to measure an intrinsic interval of the ventricle, which is concluded by the intrinsic depolarization, and to decrease a subsequent pacing delay of the ventricle for a subsequent cardiac cycle to be less than or equal to the measured intrinsic interval, wherein to measure the intrinsic interval and to decrease the subsequent pacing delay are performed on a beat by beat basis.

2. The cardiac therapy system of claim 1, wherein the pacing control circuitry is configured to further decrease the pacing delay for additional cardiac cycles until the cardiac response classification circuitry determines that capture occurs.

3. The cardiac therapy system of claim 1, wherein the pacing control circuitry is further configured to deliver the CRT pacing if an intrinsic depolarization of the ventricle is not detected during the pacing delay of the cardiac cycle, and to adjust a subsequent pacing delay of a subsequent cardiac cycle based on the cardiac pacing response of the ventricle to the delivered CRT pacing.

4. The cardiac therapy system of claim 1, further comprising a memory, configured to store information including measured cardiac rate, measured intrinsic intervals of the at least one ventricle, and cardiac pacing responses of the ventricle for a plurality of cardiac cycles, wherein the pacing control circuitry is configured to analyze the stored information to determine pacing delays for the ventricle, the analysis taking into account one or more of the measured cardiac rate, the measured intrinsic intervals, and the cardiac pacing responses of the ventricle for the plurality of cardiac cycles.

5. The cardiac therapy system of claim 4, wherein the pacing control circuitry is configured to develop a look-up table of pacing delays for the ventricle based on the analysis.

6. The cardiac therapy system of claim 4, wherein the pacing control circuitry is configured to increase the pacing delay of the ventricle by a predetermined amount during one or more additional cardiac cycles following the subsequent cardiac cycle.

7. The cardiac therapy system of claim 1, wherein the pacing control circuitry is configured to schedule the CRT pacing to both left and right ventricles, to inhibit the scheduled pace to one or both of the left and right ventricles, to measure the intrinsic intervals of one or both of the left and right ventricles, and to decrease subsequent pacing delays of one or both of the left and right ventricles.

8. The cardiac therapy system of claim 1, wherein:
the pacing control circuitry and pacing circuitry are configured to cooperate to deliver the scheduled CRT pacing if no intrinsic depolarization of the ventricle is detected during the pacing delay; and
the cardiac response classification circuitry is configured to determine a cardiac pacing response to the delivered pacing including discriminating between capture, fusion, and non-capture of the ventricle, wherein the pacing control circuitry is configured to adjust the pacing delay of the ventricle for the subsequent cardiac cycle based on the cardiac pacing response.

9. The cardiac therapy system of claim 8, wherein the pacing control circuitry is configured to maintain or increase the pacing delay if capture is determined as the cardiac pacing response.

10. The cardiac therapy system of claim 8, wherein the pacing control circuitry is configured to decrease the pacing delay if fusion is determined as the cardiac pacing response.

11. The cardiac therapy system of claim 8, wherein the pacing control circuitry is configured to measure cardiac rate and to adjust the pacing delay based on the measured intrinsic interval, the cardiac pacing response, and the measured cardiac rate.

12. The cardiac therapy system of claim 8, further comprising
a memory configured to store information related to the measured cardiac rate, the measured intrinsic interval, and the cardiac pacing response for a plurality of cardiac intervals; and
an external device configured to present to a clinician information indicating relationships between the measured cardiac rate, the measured intrinsic interval, and the cardiac pacing response for the plurality of cardiac intervals.

13. The cardiac therapy system of claim 12, wherein:
the pacing control circuitry is configured to analyze the stored information to determine at least one recommended pacing delay for a subsequent cardiac cycle based on the pacing delay, the measured cardiac rate, the measured intrinsic interval; and the cardiac pacing response for the plurality of cardiac intervals; and
the external device is configured to present the at least one recommended pacing delay to a human analyst via a user interface.

14. The cardiac therapy system of claim 13, wherein the at least one recommended pacing delay comprises one or more of right atrioventricular delay, a left atrioventricular delay and an interventricular delay.

15. The cardiac therapy system of claim 12 wherein the pacing control circuitry is configured to analyze the stored information to configure a look up table of recommended pacing delays based on previous pacing delays, the measured cardiac rate, the measured intrinsic interval; and the cardiac pacing response for the plurality of cardiac intervals.

16. The cardiac therapy system of claim 1, further comprising a sensor configured to generate an output based a patient's hemodynamic need, wherein the pacing control circuitry is further configured to adjust the pacing delay based on the sensor output.

17. The cardiac therapy system of claim 11, wherein the pacing control circuitry is configured to adjust the pacing delay based on a look-up table indexed by cardiac rate.

18. The cardiac therapy system of claim 11, wherein the pacing control circuitry is configured to adjust one or more pacing energy parameters if the cardiac response is determined to be non-capture.

19. The system of claim 1, wherein the pacing control circuitry comprises a controller, and the controller is configured to determine if capture of the ventricle occurs for the subsequent cardiac cycle.

20. The system of claim 19, wherein the controller is configured to further decrease the pacing delay for additional cardiac cycles until the device determines that capture occurs.

21. The system of claim 19, wherein the controller is further configured to deliver the CRT pacing if an intrinsic depolarization of the ventricle is not detected during the pacing delay of the cardiac cycle, and to adjust a subsequent pacing delay of a subsequent cardiac cycle based on the cardiac pacing response of the ventricle to the delivered CRT pacing.

22. The system of claim 19, wherein the memory is further configured to store information including measured cardiac rate, measured intrinsic intervals of the at least one ventricle, and cardiac pacing responses of the ventricle for a plurality of cardiac cycles, wherein the device is configured to analyze the stored information to determine pacing delays for the ventricle, the analysis taking into account one or more of the measured cardiac rate, the measured intrinsic intervals, and the cardiac pacing responses of the ventricle for the plurality of cardiac cycles.

23. The system of claim 22, wherein the device is configured to develop a look-up table of pacing delays for the ventricle based on the analysis.

24. The system of claim 22, wherein the controller is configured to increase the pacing delay of the ventricle by a predetermined amount during one or more additional cardiac cycles following the subsequent cardiac cycle.

25. The system of claim 19, wherein the controller is configured to schedule the CRT pacing to both left and right ventricles, to inhibit the scheduled pace to one or both of the left and right ventricles, to measure the intrinsic intervals of one or both of the left and right ventricles, and to decrease subsequent pacing delays of one or both of the left and right ventricles.

26. The system of claim 19, wherein:
the controller is configured to deliver the scheduled CRT pacing if no intrinsic depolarization of the ventricle is detected during the pacing delay; and
the system is configured to determine the cardiac pacing response to the delivered pacing including discriminating between capture, fusion, and non-capture of the ventricle, wherein the controller is configured to adjust the pacing delay of the ventricle for the subsequent cardiac cycle based on the cardiac pacing response.

27. The system of claim 26, wherein the controller is configured to maintain or increase the pacing delay if capture is determined as the pacing response.

28. The system of claim 26, wherein the controller is configured to decrease the pacing delay if fusion is determined as the pacing response.

29. The system of claim 26, wherein the memory is further configured to store information related to the measured cardiac rate, the measured intrinsic interval, and the cardiac pacing response for a plurality of cardiac intervals, the system further comprising:
an external device configured to present to a clinician information indicating relationships between the measured cardiac rate, the measured intrinsic interval, and the cardiac pacing response for the plurality of cardiac intervals.

30. The system of claim 19, further comprising a sensor configured to generate an output based a patient's hemodynamic need, wherein the controller is further configured to adjust the pacing delay based on the sensor output.

* * * * *